(12) United States Patent
Mikhailov et al.

(10) Patent No.: US 9,284,835 B2
(45) Date of Patent: Mar. 15, 2016

(54) METHOD FOR MEASUREMENT OF WEIGHT CONCENTRATION OF CLAY IN A SAMPLE OF A POROUS MATERIAL

(71) Applicant: SCHLUMBERGER TECHNOLOGY CORPORATION, Sugar Land, TX (US)

(72) Inventors: Dmitry Mikhailov, Moscow (RU); Valery Vasilievich Shako, Moscow (RU); Evgeny Chuvilin, Moscow (RU); Evgeny Samarin, Moscow (RU)

(73) Assignee: Schlumberger Technology Company, Sugar Land, TX (US)

( * ) Notice: Subject to any disclaimer, the term of this patent is extended or adjusted under 35 U.S.C. 154(b) by 153 days.

(21) Appl. No.: 14/015,943

(22) Filed: Aug. 30, 2013

(65) Prior Publication Data

US 2014/0065713 A1    Mar. 6, 2014

(30) Foreign Application Priority Data

Sep. 3, 2012  (RU) ................................. 2012137228

(51) Int. Cl.
| | | |
|---|---|---|
| *G01N 33/24* | (2006.01) | |
| *G01N 5/00* | (2006.01) | |
| *E21B 49/00* | (2006.01) | |

(52) U.S. Cl.
CPC ............ *E21B 49/005* (2013.01); *G01N 33/241* (2013.01); *G01N 5/00* (2013.01)

(58) Field of Classification Search
CPC ........ G01N 33/241; G01N 5/00; G01N 33/24
USPC .......... 378/4–6; 436/25, 27–28, 30–31; 702/8
See application file for complete search history.

(56) References Cited

U.S. PATENT DOCUMENTS

| | | | | |
|---|---|---|---|---|
| 4,352,674 A | * | 10/1982 | Fery ................................ | 436/27 |
| 4,540,882 A | | 9/1985 | Vinegar et al. | |
| 4,688,238 A | * | 8/1987 | Sprunt et al. ...................... | 378/4 |
| 4,691,772 A | * | 9/1987 | Ebenhack et al. ........ | 166/250.02 |
| 4,722,095 A | | 1/1988 | Muegge et al. | |
| 4,744,919 A | * | 5/1988 | O'Holleran ........ | G01N 33/0011 239/2.1 |
| 4,782,501 A | * | 11/1988 | Dixon, Jr. ......................... | 378/4 |
| 4,797,906 A | * | 1/1989 | Smith .............................. | 378/44 |
| 4,799,382 A | * | 1/1989 | Sprunt et al. ................ | 73/152.07 |
| 4,982,604 A | * | 1/1991 | Davis et al. .................. | 73/152.11 |
| 5,027,379 A | | 6/1991 | Hunt et al. | |
| 5,036,193 A | * | 7/1991 | Davis et al. .................... | 250/255 |
| 5,063,509 A | * | 11/1991 | Coles et al. .................... | 702/23 |
| 5,086,643 A | * | 2/1992 | Marek .............................. | 73/38 |
| 5,244,958 A | * | 9/1993 | Goodman ...................... | 524/447 |
| 5,253,719 A | | 10/1993 | Blauch et al. | |
| 5,297,420 A | * | 3/1994 | Gilliland et al. ................. | 73/38 |
| 5,331,155 A | * | 7/1994 | Blauch .......................... | 250/255 |
| 6,009,747 A | | 1/2000 | dos Santos | |
| 6,220,371 B1 | * | 4/2001 | Sharma et al. .................... | 175/50 |
| 6,912,898 B2 | * | 7/2005 | Jones et al. ................. | 73/152.11 |
| 7,589,050 B2 | | 9/2009 | Frenier et al. | |
| 7,888,416 B2 | * | 2/2011 | Tamura et al. ................. | 524/175 |
| 8,420,040 B2 | * | 4/2013 | Tamura et al. .............. | 423/328.3 |
| 8,761,334 B2 | * | 6/2014 | Mikhailov ............. | G01N 33/24 378/53 |
| 8,873,701 B2 | * | 10/2014 | Mikhailov et al. ................. | 378/4 |
| 8,938,045 B2 | * | 1/2015 | Dvorkin et al. .................... | 378/4 |
| 2007/0259992 A1 | * | 11/2007 | Tamura et al. ................. | 523/210 |
| 2009/0227715 A1 | * | 9/2009 | Tamura et al. ................. | 524/175 |
| 2013/0010918 A1 | | 1/2013 | Mikhailov et al. | |
| 2013/0010919 A1 | * | 1/2013 | Mikhailov ............. | G01N 33/24 378/19 |
| 2013/0182819 A1 | * | 7/2013 | Dvorkin et al. ................... | 378/5 |
| 2014/0060172 A1 | * | 3/2014 | Mikhailov ........... | G01N 15/082 73/152.07 |
| 2014/0064452 A1 | * | 3/2014 | Mikhailov ........... | G01N 23/207 378/71 |

FOREIGN PATENT DOCUMENTS

GB         1250186         10/1971

OTHER PUBLICATIONS

Whilte, N. G. et al, Clays and Clay Minerals 1982, 30, 375-382.*
Amaefule, J. O. et al, Petroleum Society of CIM, Paper No. 88-39-65, 36 pages.*
Beatty, T. et al, Oil & Gas Journal 1993, 91, 64-70.*
Bain, D. C. et al, "Chemical analysis" in Clay Mineralogy: Spectroscopic and Chemical Determinative Methods Willson, M. J., editor, 1994, Chapman & Hall, London, 300-332.*
Ugbo, J. et al, SPE-113031-STU 2007, 11 pages.*
Marsala, A. F. et al, SPE 143468 2011, 6 pages.*
van Overveldt, A. S. et al, SPE 151856 2012, 25 pages.*
Eylem, C. et al, Analyst 1989, 114, 351-353.*
Francis, P. A. et al, SPE 30088, 1995, 101-115.*
Longeron, D. et al, SPE 30089, 1995, 117-131.*
Rosario, F. et al, Journal of Colloid and Interface Science 1996, 181, 1-10.*

(Continued)

*Primary Examiner* — Arlen Soderquist

(57) ABSTRACT

Determining weight concentration of clay in a sample of a porous material, a water-soluble salt of a metal is selected that enters in a selective ion exchange reaction with clay, with the general formula $R^+M^-$, where a metal $R^+$ is selected from the group $\{Ba^{2+}; Sr^{2+}; Tl^+; Rb^+ \ldots \}$, $M^-$ is selected from the group $\{Cl_n; NO_n; OHn; CH3COO, SO_4; \ldots \}$ in accordance with the table of solubility of inorganic substances in water. Clay is marked by means of mixing the clay with a water solution of the selected salt of the metal, residues of the salt of the metal that have not interacted with the clay are removed. X-ray fluorescent spectrometry of the marked clay and of the sample is conducted and content of the metal in the marked clay and natural content of the metal in the sample are determined. A water solution of the marked clay is pumped through the sample, the sample is dried and X-ray fluorescent spectrometry of the entire sample or of its individual segments is conducted. Content of the metal in the sample or in each segment is determined and weight concentrations of clay retained in the sample or in each of its segments are determined.

4 Claims, 1 Drawing Sheet

(56) References Cited

OTHER PUBLICATIONS

Liu, X. et al, SPE Formation Evaluation Mar. 1996, 26-30.*
Shaw, J. C. et al, SPE 37121, 1996, 713-722.*
Bishop, S. R., SPE 38156 1997, 21 pages.*
Argillier, J. F. et al, SPE Drilling & Completion Dec. 1999, 14, 266-273.*
Shahwan, T. et al, Journal of Radioanalytical and Nuclear Chemistry 2002, 254, 563-568.*
Atun, G. et al, Radiochimica ACTA 2003, 51, 223-228.*
Shahwan, T. et al, Journal of Radioanalytical and Nuclear Chemistry 2004, 260, 43-48.*
Neto, J. C. Q. et al, SPE 95025, 2005, 8 pages.*
Tournassat, C. et al, Soil Science Society of America Journal 2009, 73, 928-943.*
Karaguzel, C. et al, Applied Clay Science 2010, 48, 398-404.*
Alotaibi, M. B. et al, SPE Drilling & Completion Jun. 2010, 253-262.*

* cited by examiner

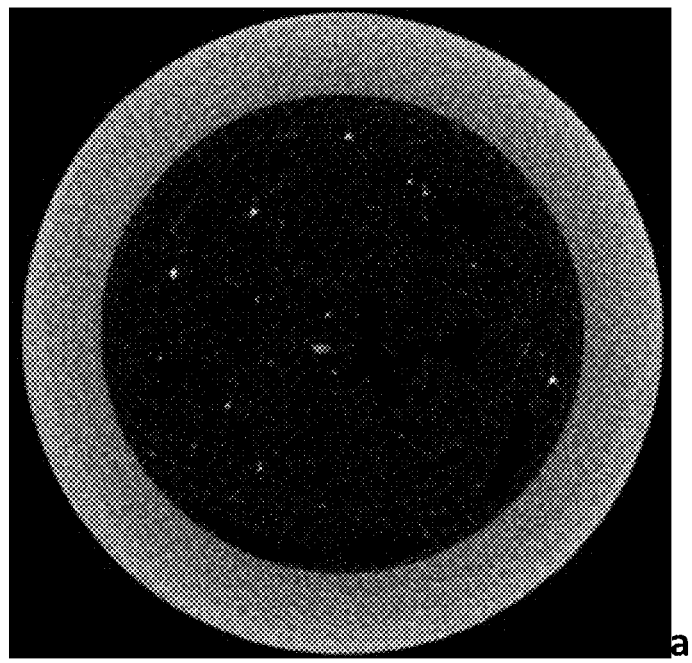
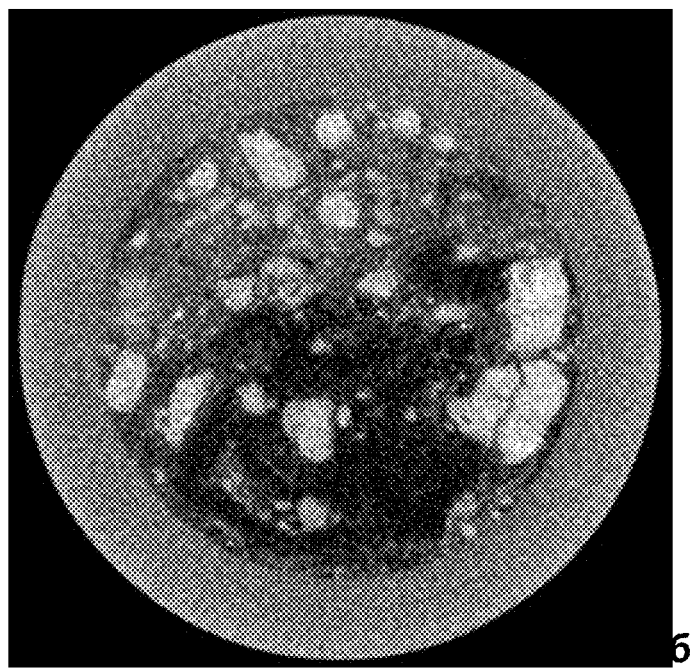

METHOD FOR MEASUREMENT OF WEIGHT CONCENTRATION OF CLAY IN A SAMPLE OF A POROUS MATERIAL

CROSS-REFERENCE TO RELATED APPLICATION

This application claims priority to Russian Application No. 1012137228 filed Sep. 3, 2012, which is incorporated herein by reference in its entirety.

FIELD

The subject disclosure relates to methods of non-destructive testing of samples of porous materials, in particular, it may be used for quantitative examination of the deterioration of properties of oil/gas containing formations ("formation damage") due to invasion, in the process of drilling clayey materials contained in a drilling mud.

SUMMARY

The problem of formation damage under the impact of drilling mud (or flushing liquid) is very important, especially for long horizontal wells, because most of them have open-hole completions, i.e., without cemented and perforated production casing.

Drilling muds are complex mixtures of clay, small particles (with dimensions from several millimeters to less than one micron) and organic additives (polymers, surfactants, etc.) contained in a 'carrier' liquid—the 'base' of the drilling mud being water, oil or some synthetic liquid.

In the process of drilling under the action of excess pressure, drilling mud filtrate as well as small particles and clay contained in it invade into the near-borehole zone of a formation and cause a considerable decrease of its permeability (for characterizing this phenomenon, the term 'damage of the near-borehole zone of formation' or simply 'formation damage' is used).

During the technological procedure of clean-out of the well (by means of gradual putting on production), these components are partly flowed back from the near-borehole zone and its permeability is partly restored. Nonetheless, part of these components remain retained in the pore space (adsorption on pore surfaces, capture in pore channel bottlenecks, etc.), that result in a considerable difference between the initial permeability and the permeability restored after performance of the technological procedure of clean-out (a value of restored permeability usually does not exceed 50-70% of the initial one).

The generally accepted laboratory method for quality control of a drilling mud is the filtration experiment comprising injecting drilling mud into a core sample with subsequent back-pumping of it (i.e., displacement of the invaded drilling mud with the initial formation fluid by injecting it from the opposite end of the core sample), in the course of this experiment the dynamics of deterioration/restoration of permeability is measured as a function of the number of injected pore volumes of fluids (drilling mud or formation fluid).

However, the concentration of clay and other components of a drilling mud retained in the pore space after back-pumping is important information for understanding the mechanism of formation damage and selecting an appropriate method for enhancement of productivity index of a well (minimization of damage to the near-borehole zone of the formation). These parameters are not measured within the framework of the above-mentioned procedure of quality check of drilling mud.

Quantitative analysis of formation damage mechanisms associated with invasion of clayey materials in the process of drilling is of highest interest due to wide-spread usage of drilling muds on clay base.

Weight concentration of clay penetrated into the pore space in the course of impact of drilling mud is usually low (does not exceed 1-1.5% by weight). Nonetheless, due to a high swelling factor of clay and porosity, such low weight concentration results in a considerable (5-20 times) reduction of rock permeability.

The technical problem is associated with the difficulty of measuring a low concentration of clay in a porous medium, because X-ray diffraction analysis and X-ray computer tomography do not provide sufficient resolution for weight concentrations of a material <1%.

Clay has a low contrast to X-ray radiation and cannot be resolved with the required accuracy.

In U.S. Pat. No. 4,540,882, as well as U.S. Pat. No. 5,027,379, methods are disclosed for determining invasion depth of a drilling mud with the use of X-ray computer tomography of a core with addition of a contrast agent. Utilization of a contrast agent soluble in the 'carrier fluid' does not make it possible to evaluate the depth of penetration and concentration of clay and other low-contrast additives contained in the drilling mud, because depth of invasion of drilling mud filtrate and of the said additives in the general case are different.

In U.S. Pat. No. 5,253,719, a method is suggested for diagnosing formation damage by means of analyzing radially oriented core samples taken from a well. Core samples are analyzed with the use of a set of different analytical methods for determining the type and the degree of formation damage, as well as the depth of the damaged zone. Among the analytical methods listed are X-ray diffraction (XRD) analysis, scanning electronic microscopy (SEM), back-scatter electronic microscopy, petrographic analysis, and optical microscopy.

However, the methods listed in the above-mentioned patent are not applicable for measurement of a low concentration of clay (weight concentration less than 1%).

The technical result achieved in realization of the claimed invention includes providing for the possibility to measure a low concentration of clay penetrated in the pore space of a sample in the course of injection of a drilling mud.

In accordance with the claimed method for determining weight concentration of clay in a sample of a porous medium, selected is a water-soluble salt of a metal that enters into a selective ion exchange reaction with clay, with the general formula $R^+M^-$, where a metal $R^+$ is selected from the group $\{Ba^{2+}; Sr^{2+}; Tl^+; Rb^+ \ldots \}$, $M^-$ is selected from the group $\{Cl_n^-; NO_n^-; OHn; CH3COO, SO_4; \ldots\}$ in accordance with the table of solubility of inorganic substances in water. Clay is marked by means of mixing the clay with a water solution of the selected metal salt, then residues of the metal salt that have not reacted with clay are removed. X-ray fluorescent spectrometry of the marked clay and of the sample of the porous material is conducted, and content of the metal in the marked clay and natural content of the metal in the sample are determined, respectively. Then a solution of clay with a concentration is prepared by means of mixing the marked clay with water, and the prepared water solution of the marked clay is pumped through a sample of a porous material. The sample is dried, X-ray fluorescent spectrometry of the sample of the porous material is conducted again and a concentration of the metal in the sample is determined, and after that weight concentration of clay in the sample of the porous material is calculated as $$n_{cl} = \frac{\eta_\Sigma - \eta_n}{\eta_{cl} - \eta_n}$$

where $\eta_\Sigma$ is content of the metal in the sample of the porous material after pumping through the sample of water solution of the marked clay, $\eta_{cl}$ is content of the metal in the marked clay, $\eta_n$ is natural content of the metal in the sample of the porous material.

In other embodiments, a water-soluble salt of a metal is selected entering into a selective ion exchange reaction with clay, with the general formula $R^+M^-$, where a metal $R^+$ is selected from the group $\{Ba^{2+}; Sr^{2+}; Tl^+; Rb^+ \ldots \}$, $M^-$ is selected from the group $\{Cl_n; NO_n; OHn; CH3COO, SO_4; \ldots \}$ in accordance with the table of solubility of inorganic substances in water. Clay is marked by mixing the clay with a water solution of the selected salt of the metal. Then, the residues of the salt that have not interacted with the clay are removed. X-ray fluorescent spectrometry of the marked clay and of the sample of the selected porous medium is conducted and content of the metal in the marked clay and natural content of the metal in the sample are determined, respectively. A solution of the marked clay with a concentration is prepared by mixing the marked clay with water and the prepared water solution of the marked clay is pumped through the sample of the porous material. The sample is dried and divided into at least two segments. X-ray fluorescent spectrometry of each segment is conducted, content of the metal in each segment is determined and weight concentrations of clay retained in each sample of the porous material are calculated as $$n_{cl}^i = \frac{\eta_\Sigma^i - \eta_n}{\eta_{cl} - \eta_n}$$

where $n_{cl}^i$ is weight concentration of the clay in the $i^{th}$ segment, $\eta_\Sigma^i$ is content of the metal in each segment, $\eta_{cl}$ is content of the metal in the marked clay, $\eta_n$ is natural content of the metal in the sample of the porous material.

Residues of the salt of the metal that have not interacted with the clay may be removed by pressing-out and subsequent drying of the marked clay.

BRIEF DESCRIPTION OF THE DRAWINGS

The subject disclosure is further described in the detailed description which follows, in reference to the noted plurality of drawings by way of non-limiting examples of the subject disclosure, in which like reference numerals represent similar parts throughout the several views of the drawings, and wherein:

FIG. 1 depicts data of an X-ray computer tomography presented for a water solution of original clay and for water solution of clay mixed with water solution of selected salts of metal ($BaCl_2$).

DETAILED DESCRIPTION

The particulars shown herein are by way of example and for purposes of illustrative discussion of the examples of the subject disclosure only and are presented in the cause of providing what is believed to be the most useful and readily understood description of the principles and conceptual aspects of the subject disclosure. In this regard, no attempt is made to show structural details in more detail than is necessary, the description taken with the drawings making apparent to those skilled in the art how the several forms of the subject disclosure may be embodied in practice. Furthermore, like reference numbers and designations in the various drawings indicate like elements.

The method of measurement of weight concentration of clay in a porous material is implemented as follows.

Clay is preliminarily 'marked' by means of mixing with a water solution of a salt of a special marker metal. For marking of clay, a soluble salt of metal is selected that enters into a selective ion exchange reaction with the clay under investigation. As a result of an ion exchange reaction, ions of the marker metal are accumulated on the clay, thus 'marking' it.

In the general form the formula for a water-soluble salt of a metal can be written in the form: $R^+M^-$, where the substances $R^+$ and $M^-$ are selected in accordance with the table of solubility of inorganic substances in water: $R^+$ is a metal $\{Ba^{2+}; Sr^{2+}; Tl^+; Rb^+ \ldots \}$; $M^-$ is a substance $\{Cl_n; NO_n; OHn; CH3COO, SO_4; \ldots \}$.

Then by pressing-out and subsequent drying of the marked clay (or by another possible method) residues of the salt of the marker metal that have not interacted with the clay are removed.

X-ray fluorescent spectrometry is conducted (in accordance with the generally accepted technique, see, for example, Верховодов П. А. Рентгеноспектральный анализ : Вопросы теории и способы унификации . Киев : Наукова думка , 1984, 160 с. или Афонин В. П. уничева Т. Н. Рентгеноспектральный флуоресцентный анализ горных пород и минералов . Новосибирск : Наука, 1977, 256 с [Verkhovodov P. A. *X-ray spectral analysis: Issues of theory and methods of unification*. Kiev: Naukova Dumka, 1984, 160 p., or Afonin V. P., Gunicheva T. N. *X-ray spectral fluorescent analysis or rocks and minerals*. Nopvosibirsk: Nauka, 1977, 256 p.].) of the marked clay for measurement of content of the metal $\eta_{cl}$. X-ray fluorescent spectrometry of a representative part of the initial sample of the porous material is conducted for measurement of the natural content of the metal $\eta_n$.

A solution of the marked clay with a concentration is prepared by mixing the marked clay with water.

Pumping of a water solution of the marked clay through the sample of the porous material is conducted and after that X-ray fluorescent spectroscopy of a representative part of the sample of the porous material is conducted for determining content of the metal $\eta_\Sigma$.

Weight concentration of the clay is determined in accordance with the following formula:

$$n_{cl} = \frac{\eta_\Sigma - \eta_n}{\eta_{cl} - \eta_n} \text{ГДе}$$

$$n_{cl} = \frac{m_{cl}}{m_\Sigma}$$

This formula for calculating weight concentration of the marked clay in the porous material follows from the condition of additivity of an increase of concentration of the marker metal in the sample of the porous material with an increase of concentration (by mass) of the marked clay:

$$\eta_\Sigma m_\Sigma = \eta_n m_n + \eta_{cl} m_{cl} \qquad (1)$$

where $m_n$ and $\eta_n$ are mass of the metal and content of the metal in the sample of the porous material before pumping-through of the clay-containing solution; and $m_{cl}$ and $\eta_{cl}$ are mass of the metal and content of the metal in the marked clay; $m_\Sigma$ and $\eta_\Sigma$ are mass of the metal and content of the metal in the sample of the porous material after pumping-through the solution of the marked clay.

Combining the relationship (1) with the mass balance $$m_\Sigma = m_n + m_{2\pi} \quad (2)$$

makes it possible to determine concentration of the clay $n_{cl}$ in the sample with known $\eta_n$, $\eta_{cl}$ and $\eta_\Sigma$:

$$n_{cl} = \frac{\eta_\Sigma - \eta_n}{\eta_{cl} - \eta_n} \text{ГД} e \quad (3)$$

$$n_{cl} = \frac{m_{cl}}{m_\Sigma}$$

As an example, let us consider utilization of the suggested method for calculating weight concentration of clay retained in the pore space after the cycle direct pumping—back pumping of a model drilling mud (1% water solution of bentonite clay) through a sample of a porous material.

Taking into consideration the composition of bentonite clay $Al_2[Si_4O_{10}](OH)_2 \cdot nH_2O$ and following the standard table of solubility of inorganic substances in water, $BaCl_2$ was selected as the salt of the metal.

Water solution of the selected salt of the marker metal was mixed with the original bentonite clay. By means of pressing-out and subsequent drying of the marked clay, removal of residues of the salt of the marker metal that has not interacted with the clay was made. For illustration, FIG. 1 shows data of computer X-ray microtomography of a water solution of the original (not marked) clay and of a water solution of the marked clay (i.e., the clay that was subjected to the ion exchange reaction with the salt $BaCl_2$).

X-ray fluorescent spectrometry of the marked clay was conducted for measuring content $\eta_{cl}$ of the marker metal (Ba), as well as X-ray fluorescent spectrometry of a representative part of the sample of the porous material for measuring the natural content $\eta_n$ of the marker metal (Ba).

A 1% water solution of the marked clay was prepared by means of mixing the latter with water in the appropriate proportion.

A filtration experiment was conducted by pumping 1% water solution of the marked clay through the sample of the porous material and subsequent back-pumping (i.e., displacement of the penetrated clay solution (clay mud) with the initial formation fluid by means of injection of it from the opposite end of the core sample).

The sample of the porous material was the divided (by means of splitting, sawing, or other methods of cutting) into four segments and consecutive numbering of the segments was made, starting from the end into which injection of the 1% water solution of the marked clay was made.

X-ray fluorescent spectrometry of representative parts of each segment of the sample of the porous material was conducted for determining content $\eta_\Sigma^i$ of the marker metal (Ba) in each $i^{th}$ segment (i=1, . . . , 4).

Using contents of the metal in the marked clay $\eta_{cl}$, in the initial sample of the porous material $\eta_n$ measured at the previous stages, and also in each $i^{th}$ segment $\eta_\Sigma^i$ of the sample of the porous medium after pumping of the 1% solution of the marked clay and subsequent back-pumping, weight concentrations $n_{cl}^i$ of clay retained in each $i^{th}$ segment of the sample of the porous material were calculated by the formula similar to Formula (3)

$$n_{cl}^i = \frac{\eta_\Sigma^i - \eta_n}{\eta_{cl} - \eta_n}$$

Knowing weight concentrations $n_{cl}^i$ of clay in each $i^{th}$ segment and distance of this segment from the input end (into which pumping of the 1% solution of the marked clay was made), it is possible to obtain the distribution of weight concentration of the clay retained in the pore space after the filtration experiment.

The invention claimed is:

1. A method for determining weight concentration of clay in a sample of a porous material comprising:
   selecting a water-soluble salt of a metal, the salt entering into a selective ion exchange reaction with clay and having a general formula $R^+M^-$, where a metal $R^+$ and an anion $M^-$ are selected in accordance with the table of solubility of inorganic substances in water so as to provide the water-soluble salt of a metal,
   marking clay by mixing the clay with a water solution of the selected water-soluble salt of the metal,
   removing residues of the salt that have not interacted with the clay,
   performing X-ray fluorescent spectrometry of the marked clay and the sample of the porous material and determining a content of the metal in the marked clay and a natural content of the metal in the sample of the porous material respectively,
   preparing a solution of the marked clay of the required concentration by means of mixing the marked clay with water,
   pumping the prepared water solution of the marked clay into the sample of the porous material,
   drying the sample,
   performing X-ray fluorescent spectrometry of the sample of the porous material and determining a content of the metal in the sample, and
   calculating weight concentration of clay in the porous material as $$n_{cl} = \frac{\eta_\Sigma - \eta_n}{\eta_{cl} - \eta_n}$$

where $\eta_\Sigma$ is the content of the metal in the sample of the porous material after pumping into the sample of the water solution of the marked clay, $\eta_{cl}$ is the content of the metal in the marked clay, $\eta_n$ is the natural content of the metal in the sample of the porous material.

2. A method of claim 1 wherein the residues of the salt of the metal that have not interacted with the clay are removed by pressing-out and subsequent drying of the marked clay.

3. A method for determining weight concentration of clay in a sample of a porous material comprising:
   selecting a water-soluble salt of a metal, the salt entering into a selective ion exchange reaction with clay and having with the general formula $R^+M^-$, where a $R^+$ metal and an anion $M^-$ are selected in accordance with the table of solubility of inorganic substances in water so as to provide the water-soluble salt of a metal, marking clay by mixing the clay with a water solution of the selected water-soluble salt of the metal, removing residues of the salt of the metal that have not interacted with the clay, performing X-ray fluorescent spectroscopy of the marked clay and the sample of the porous material and determining a content of the metal in the marked clay and a natural content of the metal in the sample of the porous material respectively, preparing a solution of the marked clay with the required concentration by mixing the marked clay with water, pumping the prepared water solution of the marked clay through the sample of the porous material, drying the sample, dividing the sample into at least two segments, performing X-ray fluorescent spectroscopy of each segment and determining a content of the metal in each segment and calculating weight concentrations of clay retained in each segment of the porous material as $$n_{cl}^i = \frac{\eta_\Sigma^i - \eta_n}{\eta_{cl} - \eta_n}$$

where $n_{cl}^i$ is weight concentration of clay in the $i^{th}$ segment, $\eta_\Sigma^i$ is the content of the metal in the $i^{th}$ segment, $\eta_{cl}$ is the content of the metal in the marked clay, $\eta_n$ is the natural content of the metal in the sample of the porous material.

4. A method of claim 3 wherein the residues of the salt of the metal that have not interacted with the clay are removed by means of pressing-out and subsequent drying of the marked clay.

* * * * *